United States Patent [19]

Whitehead

[11] Patent Number: 4,526,825

[45] Date of Patent: Jul. 2, 1985

[54] FLUID PERVIOUS THERMOPLASTIC CONTAINING WEB WITH FUSED BARRIER LINES POSITIONED IN REGISTRY ON THE WEB

[75] Inventor: Howard A. Whitehead, Appleton, Wis.

[73] Assignee: Kimberly-Clark Corporation, Neenah, Wis.

[21] Appl. No.: 447,060

[22] Filed: Dec. 6, 1982

Related U.S. Application Data

[63] Continuation of Ser. No. 295,719, Aug. 24, 1981, abandoned.

[51] Int. Cl.³ .......................... B32B 3/02; B32B 5/14; A61F 13/16
[52] U.S. Cl. ...................................... 428/74; 428/194; 428/195; 428/288; 428/296; 604/366; 604/378; 604/381; 604/385 R
[58] Field of Search ............... 428/153, 154, 195, 284, 428/296, 288, 194, 192, 74, 76; 604/366, 378, 381, 385; 15/209 R, 210 R

[56] References Cited

U.S. PATENT DOCUMENTS

| | | | |
|---|---|---|---|
| 3,009,822 | 11/1961 | Drelich et al. | 428/195 |
| 3,294,091 | 12/1966 | Morse | 128/290 R |
| 4,100,324 | 7/1978 | Anderson et al. | 428/288 |
| 4,154,883 | 5/1979 | Elias | 428/296 |
| 4,265,954 | 5/1981 | Romanek | 428/195 |

Primary Examiner—Paul J. Thibodeau
Attorney, Agent, or Firm—Howard Olevsky; R. Jonathan Peters; G. E. Croft

[57] ABSTRACT

A sanitary appliance is provided which has fused barrier lines in the cover only.

The web is useful as a wrap for absorbent appliances or for toweling in which the fused barrier in each instance minimizes surface runoff and excessive wicking.

The invention also includes a process for making a sanitary appliance with the web of the subject invention.

1 Claim, 2 Drawing Figures

FLUID PERVIOUS THERMOPLASTIC CONTAINING WEB WITH FUSED BARRIER LINES POSITIONED IN REGISTRY ON THE WEB

This is a continuation of application Ser. No. 295,719, filed Aug. 24, 1981, now abandoned.

FIELD OF THE INVENTION

This invention relates to sanitary appliances and particularly to modified nonwoven wraps useful therewith.

BACKGROUND OF THE INVENTION

Sanitary appliances such as sanitary napkins, diapers and wound dressings are all made of similar construction. All of the sanitary appliances have a fluid permeable cover, an absorbent matrix and a fluid impermeable baffle. The fluid permeable cover is, of course, located adjacent the discharge orifice and is designed to rapidly pass fluid through itself and into the absorbent matrix. Occasionally, during periods of heavy discharge, particularly in the case of relatively viscous discharge fluids such as menses, the fluid may run off the surface of the cover material or wick along the various interstices rather than migrating downward into the absorbent.

This problem has been recognized and dealt with by utilizing one of the properties of the wrap. The wrap used in sanitary napkins and wound dressings, as well as diapers and incontinence pads, is traditionally a nonwoven synthetic material. The baffle utilized in these sanitary appliances is conventionally a thermoplastic sheet.

One of the approaches utilized to prevent fluid runoff is disclosed in U.S. Pat. Nos. 3,294,091 and 4,200,103 in which the thermoplastic baffle is positioned not only on the bottom of the appliance, but also along the sides and covers the longitudinal top edges. The baffle is then fused to the wrap to provide a fluid migration barrier. Fusing has also been used to seal a napkin at its edges. An example of such a napkin is disclosed in U.S. Pat. No. 4,059,114. It is also known to emboss sanitary napkins and particularly the thin napkins of the panty shield type to provide integrity to the batt of absorbent material. An example of such a napkin is disclosed in U.S. Pat. No. 3,881,490.

Prior art utilization of fusing fluid pervious wraps to fluid impervious baffles at the top portion of the napkin as described in U.S. Pat. No. 3,294,091 involves precise positioning of the fusing element and must be done after assembly of the napkin. As such, it is much more difficult to properly position all of the elements to create a uniform barrier line. Also, this approach tends to damage the absorbent capacity of the absorbent layer underneath due to the application of heat necessary for fusing. Positioning of the barrier is also dependent upon precise positioning of the baffle and the location of the barrier is also predetermined by the variety of possibilities of baffle configuration and position.

SUMMARY OF THE INVENTION

According to this invention, a sanitary appliance is provided in which the fluid permeable wrap has a prepositioned fused barrier and is fused to no other element of the sanitary appliance at the barrier position. Fusing is applied as the wrap is conveyed in web form, possibly even during the manufacturing process of the web. Fusing is, therefore, done in any predetermined pattern and in registry. Fusing of thermoplastic material is well known and how the fusing step is accomplished is not part of this inventive concept. In the case of a sanitary appliance, the fused barrier can be positioned at either the sides or the ends of the appliance after the fluid permeable wrap is applied or it can exist as a continuous barrier layer inset an appropriate distance from the outer periphery of the appliance. (In the case of sanitary napkins this distance is generally ¼" or less.)

BRIEF DESCRIPTION OF THE DRAWINGS

This invention can be more readily understood by reference to the drawings in which.

Figure 1:
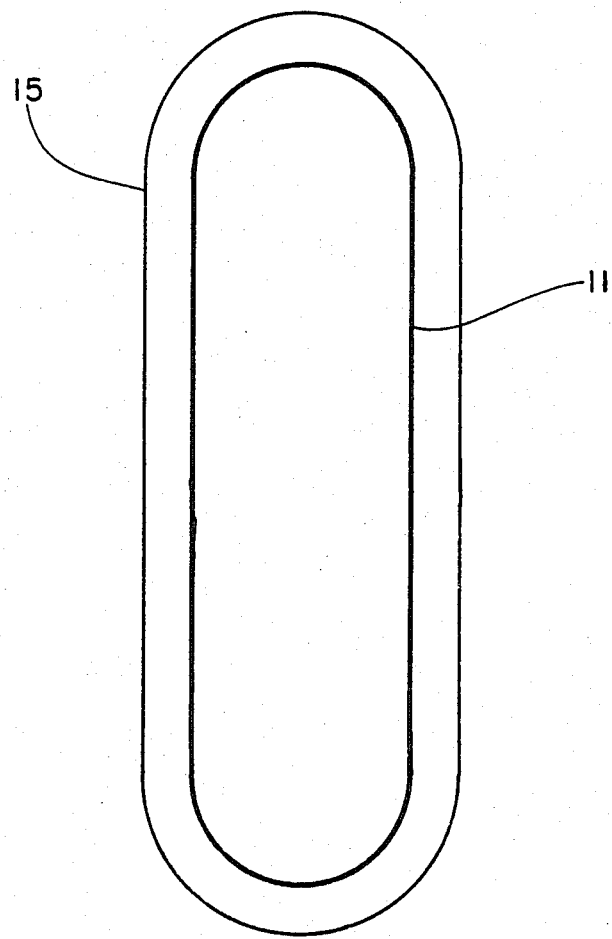
FIG. 1 is a plan view of a sanitary napkin according to the teachings of this invention; and, FIG. 2 is a plan view of embossing apparatus in conjunction with a web section showing the fused barrier lines of a cover material useful for a sanitary napkin.
Figure 2:
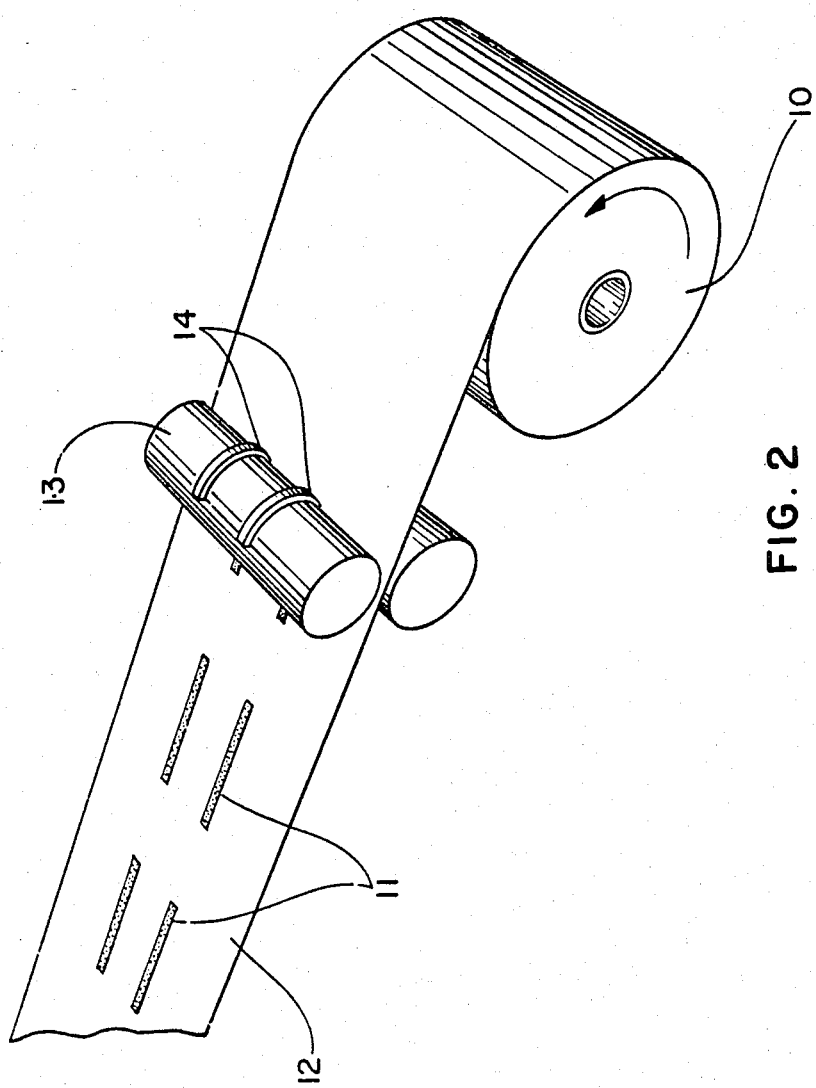

As can be seen from FIG. 2, a roll of nonwoven material 10 is driven between embossing rolls 13 having embossing areas 14. The fused barrier lines 11 placed on web 12 are positioned in registry by embossing rolls 13 so that when the web is conveyed for mating with the other components of the sanitary appliance such as a napkin, it can be wrapped and cut and positioned to provide the appropriate barrier layer in the correct configuration. A similar configuration is shown, for example, in FIG. 1 in which the barrier forms a complete inner line 11 inset from the outer periphery of the napkin 15.

This fused line tends to provide a barrier to fluid runoff and also to phenomena associated with wicking migration. This is accomplished without the process difficulties inherent in attempts to fuse the wrap while in place on a sanitary napkin.

It should be noted that other sanitary appliances such as wound dressings, diapers, incontinence garments and the like can benefit from the technology described above and all of these particular sanitary appliances are within the scope of the subject invention.

While the fluid permeable outer wrap is thermoplastic in nature it need not be completely thermoplastic and may in fact be at least partially absorbent. One particularly useful material is disclosed in U.S. Pat. No. 4,100,324 which is hereby incorporated by reference. This patent discloses a web of material formed from a merging of air streams of thermoplastic microfibers and cellulosic fibers. This airlaid web has varying absorbent capabilities depending upon the amount of cellulosic material present therein. In the case of this coformed airlaid material, fusing, is an aid to the integrity of the web itself.

In another embodiment of this invention, where an absorbent cover material is utilized such as that disclosed in U.S. Pat. No. 4,100,324, an absorbent towel can be produced in which the liquid is essentially completely retained within a defined area away from the edges of the towel. This concept is also within the ambit of the subject invention.

While the coformed airlaid material has absorbent properties and has certain specific advantages, any thermoplastic fluid previous wrap can be used according to the teachings of the subject invention. The specific properties of the fusible thermoplastic web are, of course, based upon its ultimate use.

What is claimed is:

1. In a wrapped absorbent article having in combination an absorbent batt, a fluid pervious baffle and a fluid permeable wrap containing fusible thermoplastic fibers overlying said absorbent batt, said wrap only having a pre-applied fused peredetermined continuous barrier pattern, said pattern positioned near and corresponding to the periphery of the wrapped absorbent article.

* * * * *